United States Patent [19]

Wells

[11] Patent Number: 4,514,567
[45] Date of Patent: * Apr. 30, 1985

[54] PROCESS FOR PREPARING TRIETHYLENEDIAMINE

[75] Inventor: James E. Wells, Ardmore, Pa.

[73] Assignee: Air Products and Chemicals, Inc., Allentown, Pa.

[*] Notice: The portion of the term of this patent subsequent to Sep. 20, 2000 has been disclaimed.

[21] Appl. No.: 487,789

[22] Filed: Apr. 22, 1983

Related U.S. Application Data

[63] Continuation-in-part of Ser. No. 278,814, Jun. 29, 1981, Pat. No. 4,405,784.

[51] Int. Cl.$^3$ ............................................. C07C 295/02
[52] U.S. Cl. ...................................................... 544/352
[58] Field of Search ........................................ 544/352

[56] References Cited

U.S. PATENT DOCUMENTS

| | | | |
|---|---|---|---|
| 2,467,205 | 4/1949 | Gresham et al. | 260/268 |
| 2,937,176 | 5/1960 | Herrick | 260/268 |
| 2,985,658 | 5/1961 | Krause | 260/268 |
| 3,166,558 | 1/1965 | Mascioli | 260/268 |
| 3,172,891 | 3/1965 | Brader et al. | 260/268 |
| 3,297,701 | 1/1967 | Brader et al. | 260/268 |
| 3,342,820 | 9/1967 | Brader | 260/268 |
| 3,541,172 | 11/1970 | Stowe et al. | 260/669 |
| 3,957,900 | 5/1976 | Welsang et al. | 260/681 |
| 4,036,881 | 7/1977 | Brennan et al. | 260/583 |
| 4,049,657 | 9/1977 | Brennan et al. | 260/268 |
| 4,092,316 | 5/1978 | Nieh | 544/351 |
| 4,095,022 | 6/1978 | Brennan et al. | 544/87 |
| 4,103,087 | 7/1978 | Brennan | 544/78 |
| 4,117,227 | 9/1978 | Brennan | 544/170 |

FOREIGN PATENT DOCUMENTS

| | | |
|---|---|---|
| 1494886 | 12/1977 | United Kingdom . |
| 525681 | 1/1977 | U.S.S.R. . |

OTHER PUBLICATIONS

Richard A. Nyquist & Ronald O. Kagel; Infared Spectra of Inorganic Compounds; 1971; p. 163.

*Primary Examiner*—Robert W. Ramsuer
*Attorney, Agent, or Firm*—Richard A. Dannells, Jr.; Russell L. Brewer; James C. Simmons

[57] ABSTRACT

Strontium pyro-, monohydrogen, and dihydrogen phosphates are employed as catalysts for acid catalyzed organic condensation reactions. High conversion and exceptionally high selectivity are obtained by use of such catalysts in cyclization reactions such as in the conversion of hydroxyethylpiperazine to triethylenediamine.

4 Claims, No Drawings

PROCESS FOR PREPARING TRIETHYLENEDIAMINE

CROSS REFERENCE TO RELATED APPLICATION

This is a continuation-in-part of Ser. No. 278,814, filed June 29, 1981 and now U.S. Pat. No. 4,405,784.

TECHNICAL FIELD OF THE INVENTION

The present invention relates to organic condensation reactions effected in the presence of solid acidic catalyst and is more particularly concerned with the production of bicyclo N-heterocyclic compounds in enhanced yields.

BACKGROUND OF THE PRIOR ART

Organic synthesis by condensation reactions resulting in the loss of a molecule of water or of ammonia are well known in the art. Certain of such reactions are generally effected in the presence of acidic catalysts. An important area in which such acid catalysis has been employed is in cyclization reactions as in the synthesis of triethylene diamine and its C-substituted homologues. The catalysts more generally used or proposed for use in such cyclization reactions are solid products of the Lewis acid type.

Triethylenediamine, also called diazabicyclo-[2.2.2.]-octane, has been widely employed commercially as a catalyst in organic isocyanate reactions with compounds containing labile hydrogen, as in the production of urethane polymers. Triethylenediamine (sometimes hereinafter referred to as TEDA) was initially prepared in significant quantities by methods such as that described in U.S. Pat. No. 2,937,176, by passing aliphatic amines in vapor phase over acidic cracking catalyst, such as silica-alumina dried gel or acid-activated clays. Numerous other feedstocks as well as other catalysts are disclosed in subsequent patents for preparation of TEDA as well as C-alkyl derivatives thereof.

Typical among these are U.S. Pat. Nos. 2,985,658 and 3,166,558 employing preferably silica-alumina type catalyst, but listing also other useful solid acid catalysts that can be employed such as alumina in which phosphate or fluoride ion is incorporated (U.S. Pat. No. 2,985,658).

Among other catalysts proposed in the patent art for preparation of triethylenediamine and/or C-alkyl homologues thereof, are certain phosphate compounds, particularly aluminum phosphate.

The use of aluminum phosphate as a catalyst in the preparation of heterocyclic compounds from aliphatic amines was early disclosed in U.S. Pat. No. 2,467,205, particularly for the preparation of piperazine from ethylenediamine or from polyethylene polyamine. The use of aluminum phosphate as catalyst in the preparation of triethylenediamine accompanied by piperazine among other by-products is further described in U.S. Pat. No. 3,172,891; while U.S. Pat. No. 3,342,820 describes the use of complex phosphates of alkali metal and trivalent metals in the preparation of C-alkyl TEDA.

U.S. Pat. No. 3,297,701 discloses as catalysts for preparation of TEDA and C-alkyl TEDA, in addition to the preferred aluminum phosphate stated to be superior, other phosphate compounds including calcium and iron phosphates among other listed metal phosphates. In the conversion of N-aminoethylpiperazine to triethylenediamine over aluminum phosphate catalyst, at most up to 39 mol% triethylenediamine is said to be obtained. Other of the named metal phosphate catalysts in the examples of the patent obtain yields of less than 10 mol% TEDA.

Acid metal phosphate catalysts, particularly phosphates of boron, aluminum and trivalent iron, have also been proposed for use in intramolecular cyclic dehydration reactions and other condensation reactions involving amino compounds. Examples of such reactions are found in U.S. Pat. No. 4,117,227, which discloses conversion of an N-substituted diethanolamine to the corresponding N-substituted morpholine. U.S. Pat. No. 4,036,881 describes preparation of non-cyclic polyalkylene polyamines by condensation of an alkylene diamine with an ethanolamine. N-hydroxyethylmorpholine is condensed with morpholine in the presence of aluminum phosphate catalyst to form dimorpholino ethane according to U.S. Pat. No. 4,103,087. Similarly, dimorpholinodiethyl ether is obtained by condensation of hydroxyethyl morpholine with aminoethyl morpholine over iron, aluminum or boron phosphate in U.S. Pat. No. 4,095,022. Reaction of piperazine with ethanolamine over such acidic metal phosphate produces N-aminoethyl piperazine according to U.S. Pat. No. 4,049,657.

Pyrophosphates of lithium, sodium, strontium and barium have been used as dehydration catalysts; see U.S. Pat. No. 3,957,900. Phosphates and pyrophosphates of strontium and nickel have been used for the dehydrogenation of, for example, n-butene to butadiene under the conditions described in U.S. Pat. No. 3,541,172.

SUMMARY OF THE INVENTION

It has now been found that unexpectedly high yields of organic compounds such as TEDA are selectively obtained when the condensation reaction thereof is carried out in the presence of catalytic amounts of a catalyst selected from the group consisting of strontium diorthophosphate —$SrHPO_4$— (also known as strontium monohydrogen phosphate), strontium pyrophosphate —$Sr_2P_2O_7$—, strontium dihydrogen phosphate —$Sr(H_2PO_4)_2$—, and mixtures thereof. It was further found that $SrHPO_4$, $Sr_2P_2O_7$, $Sr_1(H_2PO_4)_2$ and mixtures thereof can be utilized in other acid catalyzed condensation reactions such as those which heretofore employed catalysts such as silica-alumina, aluminum phosphate or other trivalent metal phosphates.

DETAILED DESCRIPTION OF THE INVENTION

The monohydrogen and dihydrogen strontium phosphate catalysts of the present invention are prepared by reaction of a mono- or diphosphate of an alkali metal or ammonium with a soluble salt of strontium at ambient temperatures. The highest purity and best yields of the present invention are obtained when using the soluble strontium salt of a strong acid such as strontium nitrate, in substantially stiochiometric proportion to the phosphate. In aqueous media under these conditions, the reaction mixture is at a pH of about 3.5 to 6.5. In general, to obtain a precipitate of desired high content of the strontium monohydrogen or dihydrogen phosphate, the ratio of phosphate to strontium salt in the reaction mixture should be such as to have a pH of 5±3, or the mixture should be adjusted to that pH range.

The pyrophosphate form of the catalysts of the present invention are prepared by heat treating the strontium monohydrogen or dihydrogen phosphate product at temperatures above about 300° C. up to 750° C. in the presence of a mixture of steam and air, preferably at least about 20% by volume of steam.

For use as a catalyst, the strontium pyro-, monohydrogen or dihydrogen phosphate product may be employed in the form of irregular particles of the desired size range prepared by breaking up the washed and dried filter cake or in the form of regular shaped pellets obtained by known methods of casting, pelletizing or extruding or the product may be deposited or otherwise impregnated into the pores of a microporous substrate such as alumina, silica, silica-alumina, and the like. In using the catalyst of the present invention to catalyze organic condensation reactions, substantially the same conditions may be employed as when using the known catalysts for the particular synthesis. For optimum results, however, some adjustment in temperature, diluent and/or space rate may be found beneficial.

Some specific examples of the type of organic compounds selectively obtained by the method of this invention include TEDA and dimethylaminoethylmorpholine. In the production of these compounds, the temperature is in the range of about 285° to 420° C., the pressure is in the range of about 0.1 to 1.5 atmospheres, and the liquid hourly space velocity (LHSV) of the organic feed stock per volume of catalyst is in the range of about 0.05 to 1.5. Preferably depending on the particular reaction, the temperature is in the range of about 340° to 400° C., the pressure is in the range of about 0.3 to 1.0 atmospheres and the LHSV is in the range of about 0.1 to 0.3 to obtain the highest yields and most economical process. The operable ratio of the organic feeds to water diluent is about 10 to 90% on a weight basis and preferably, 20 to 60% by weight. The optimum yield of these compounds is likely to be obtained using the highest temperature in the preferred range at the lowest LHSV.

In the preparation of TEDA, the catalyst of this invention is selected from the group consisting of $SrP_2O_7$, $Sr(H_2PO_4)_2$, mixtures thereof and mixtures with $SrHPO_4$. The organic feedstock used in this reaction to produce TEDA includes mono- and di-substituted piperazines selected from the group consisting of hydroxyethylpiperazine and amonoethylpiperazine and ethanolamines and substitutes ethanolamines. The catalysts of this invention are relatively uneffected by the purity of the feedstock. For example, high conversion and good yields can be obtained from crude hydroxyethylpiperazine which contains minor quantities of piperazine and bis-hydroxyethylpiperazine.

In the preparation of dimethylaminoethylmorpholine (DMAEM), the feedstock is morpholine and dimethylethanolamine in the molar ratio in the range of about 1 to 3 and 3 to 1. Preferably, the reaction takes place in the presence of hydrogen in the molar ratio of hydrogen to organic feed of about 1 to 1 to 20 to 1 and an inert gas such as nitrogen, argon or nelium in the molar ratio of inert gas to organic feed of about 1 to 1 to 20 to 1.

CATALYSTS PREPARATION

EXAMPLE 1

200 grams of strontium nitrate [$Sr(NO_3)_2$] was dissolved in distilled water and brought to a total volume of 800 cc with distilled water. To this solution there was added 10 cc of 85% phosphoric acid followed by 34.5 cc of 50% sodium hydroxide added rapidly with vigorous stirring. The resultant fine white precipitate was stirred for 10 minutes, vacuum-filtered and water-washed. The obtained filter cake was air dried in a static oven at approximately 110° C. and broken into small ($\frac{1}{8}$ to $\frac{1}{4}$ inch) irregular pieces for evaluation.

The obtained product had a surface area of 10–15 $m^2/g$. By X-ray diffraction the principal component was identified as $\beta$-$SrHPO_4$ with minor quantities of $Sr_5(OH)(PO_4)_3$ and unreacted $Sr(NO_3)_2$. Infrared spectroscopy showed a spectrum consistent with $SrHPO_4$. (Ref: Richard A. Nygurst and Ronald O. Kagel, "Infrared Spectra of Inorganic Compounds", page 163, 1971).

EXAMPLE 2

200 grams of $Sr(NO_3)_2$ were dissolved in distilled water and diluted to 400 cc. To the obtained solution there was added with vigorous stirring a dibasic ammonium phosphate solution obtained by dissolving 36 grams of $(NH_4)_2HPO_4$ in distilled water and diluting to 400 cc. The resultant precipitate was filtered, washed with distilled water and dried in air at about 110° C.

By X-ray diffraction and infrared spectroscopy, the obtained product was shown to be essentially pure $\beta$-$SrHPO_4$.

Alpha and beta strontium hydrogen phosphate (strontium diorthophosphate) have substantially different infrared spectra and X-ray diffraction patterns, though the specific detailed crystal structures are not known. Active catalysts may be prepared from either of these crystalline forms. Fresh samples of the product generally show broad infrared bands whereas used samples have sharp infrared spectra and are clearly $\beta$-$SrHPO_4$ regardless of the form of the fresh catalyst.

EXAMPLE 3

200 grams $Sr(NO_3)_2$ was dissolved in distilled water and diluted to 400 cc. To this solution there was added a sodium phosphate solution obtained by diluting 110 grams of 85% $H_3PO_4$ with 150 cc distilled water and adding the thus diluted phosphoric acid solution (a) to (b), a solution of 151 grams 50% NaOH diluted with distilled water to 150 cc.

The resultant precipitate was filtered, washed and dried at approximately 110° C. Infrared spectroscopy showed this product to be essentially pure $\beta$-$SrHPO_4$.

EXAMPLE 4

212 grams of $Sr(NO_3)_2$ were dissolved in distilled water and diluted to 500 cc. 115 grams of ammonium dihydrogen phosphate —$NH_4H_2PO_4$— were dissolved in distilled water and diluted to 500 cc. The two salt solutions were then combined with heat and stirred for about 10 minutes. The remaining steps of the catalyst procedure for Example 1 were carried out. The resulting catalyst was believed to contain less than 5% strontium dihydrogen phosphate —$Sr(H_2PO_4)_2$— with the balance being $SrHPO_4$. The surface pH of this catalyst mixture was 4–4.6 in comparison to substantially pure strontium monohydrogen phosphate which has a surface pH of 4.8–5.4. Substantially pure strontium dihydrogen phosphate was found to have a surface pH of 0.2–1.2; see Example 7.

The resulting catalyst in the form of a fine powder was deposited on an inert, low surface area Alundum silica-alumina core using a powder-coating step. The step comprised placing the amount of catalyst to be coated into a jar with the Alundum spheres and rotating on a jar-mill for several days to cause the catalyst powder to adhere to the spheres. The resulting coated spheres contained 25% of the active catalyst and 75% inert.

EXAMPLE 5

212 grams of strontium nitrate —$Sr(NO_3)_2$— were dissolved in distilled water and diluted to 500 cc. 132 grams of dibasic ammonium phosphate —$(NH_4)_2HPO_4$— were dissolved in distilled water and diluted to 500 cc with heat. The two salt solutions were then combined with heat and stirred for about 10 minutes. The remaining catalyst preparation procedure of Example 1 was repeated and the resulting strontium monohydrogen phosphate catalyst had a surface pH of 4.8–5.2.

EXAMPLE 6

The $SrHPO_4$ catalyst of Example 5 was heat treated for 2 hours in the presence of a mixture 20% by volume steam and the balance air at 350° C. The resulting strontium pyrophosphate ($Sr_2P_2O_7$) had a crushing strength of 0.47 kg./mm of length and a packed bulk density of 1.01 kg./l.

EXAMPLE 7

132.5 grams of strontium hydroxide octahydrate —$Sr(OH)_2.8H_2O$— were dissolved in a solution of 750 cc. of 85% phosphoric acid and 1500 cc. of distilled water. The resulting solution was slowly evaporated to a total volume of about 900 cc. with the temperature being maintained at 25° to 30° C. The solution was cooled to 5° C. overnight and a white precipitate was recovered by vacuum filtration. The resulting $Sr(H_2PO_4)_2$ precipitate was washed with 5–300 cc. portions of anhydrous ethanol and with 2–200 cc. portions of anhydrous ether. The product was dried at room temperature under vacuum for 6 hours. An elemental analysis of the product showed a P/Sr mol ratio of 2.04 and the surface pH was found to be 0.2–1.2. The fine powder was pressed into tablets the size of a typical aspirin tablet and crushed to granules ⅛ to ¼ inch in size.

EXAMPLE 8

The fine powder of the catalyst prepared in accordance with Example 7 was deposited on silica-alumina spheres in a manner set forth in Example 2.

Control 2

The following salts were also combined in the manner of the Example 4 preparation:

| Salt Solutions | | Catalyst |
|---|---|---|
| (a) | (b) | Formulation |
| 106 g. $Sr(NO_3)_2$ | 40 g. 50% NaOH + 80 g. $(NH_4)_2H_2AsO_4$ | $SrHAsO_4$ |

Control 3

200 grams of $Sr(NO_3)_2$ were dissolved in distilled water and diluted to 400 cc. 92 grams of $H_2SO_4$ were diluted in 200 cc. of distilled $H_2O$. 75 grams of 50 wt. % NaOH solution were diluted to 200 cc. with distilled water. The $H_2SO_4$ and NaOH solutions were mixed together slowly. The $Sr(NO_3)_2$ solution was stirred into the solution containing $H_2SO_4$ and NaOH. The solution was stirred for 10 minutes and the precipitate was filtered, washed and dried. The surface pH of the resulting catalyst was less than 3 which was believed to be substantially all $SrSO_4$.

USE OF CATALYSTS OF EXAMPLES 1-8

EXAMPLES 9-21

Each of the products prepared in accordance with Examples 1 through 8 above and certain Controls were evaluated for catalytic performance for the preparation of TEDA with either a feed mixture containing hydroxyethylpiperazine (HEP) or N-aminoethylpiperazine (AEP) in accordance with the following test procedures:

A. 20 cc (about 6.2 g) of the catalyst was loaded into a ¾" diameter stainless steel tubular reactor.

B. The reactor was placed in a conventional tube furnace such that the catalyst bed was near the furnace center and therefore could be heated to a constant and uniform temperature.

C. The catalyst bed temperature was raised to a temperature of 320°–400° C. over a period of 15 to 30 minutes while a small flow of gaseous nitrogen was maintained through the reactor to aid in the removal of water vapor.

D. A feed mixture containing HEP or AEP and water as well as other nitrogen-containing compounds (crude hydroxyethlypiperazine, CHEP) such that the organic component made up 60% of the mixture was then allowed to flow through the catalyst bed at a rate of 6.5–7.0 cc/hour; the nitrogen flow was discontinued. Crude hydroxyethylpiperazine typically contains in addition to HEP minor quantities of bis hydroxyethylpiperazine and piperazine.

E. The catalyst bed temperture indicated in the tables set forth below was maintained during the run and the product samples were collected and analyzed. Analyses were performed using well-established gas chromatographic techniques.

The yields of TEDA and piperazine (PIP) as well as the conversion obtained from the catalysts of Examples 1–8 are compared in Tables 1 and 2 below with data from the use of a standard silica-alumina dried gel catalyst employed in the example of U.S. Pat. No. 2,985,658 (designated in Table 1 as control 1) and with control catalysts 2–5 in Table 3 below:

TABLE 1

| | EXAMPLE 9 | EXAMPLE 10 | EXAMPLE 11 | CONTROL 1 |
|---|---|---|---|---|
| Cat. of Ex. | 1* | 2* | 3 | *$SiO_2/Al_2O_3$ |
| Feed | HEP | HEP | HEP | HEP |
| Test Temp., °C. | 360 | 360 | 370 | 360 |
| HEP Conversion, Mol % | 99.3 | 99.3 | 95.4 | 100.0 |
| TEDA Yield, Mol % | 83.0 | 93.7 | 82.6 | 39.8 |
| TEDA Selectivity, Mol % | 83.6 | 94.4 | 86.6 | 39.8 |
| Wt. % Recovery | 98.5 | 98.6 | 102.1 | 94.7 |

*Average of two duplicate runs.

TABLE 2

| | | | | TEDA PRODUCTION | | | | |
|---|---|---|---|---|---|---|---|---|
| Example | Cat. of Ex. | Form | Nominal Formulation | TEDA Yield, Wt. % | PIP Yield, Wt. % | Conversion Mol. % | Temp., °C. | Feed |
| 12 | 4 | 25% Coated Spheres | SrHPO$_4$/Sr(H$_2$PO$_4$)$_2$ | 63.5 | 14.7 | 98.3 | 380 | HEP |
| 13 | 4 | 25% Coated Spheres | SrHPO$_4$/Sr(H$_2$PO$_4$)$_2$ | 18.8 | 16.4 | 77.0 | 400 | AEP |
| 14 | 5 | Granules | SrHPO$_4$[1] | 76.0 | 7.8 | 98.6 | 360 | HEP |
| 15 | 5 | Granules | SrHPO$_4$ | 29.0 | 21.0 | 99.0 | 400 | AEP |
| 16 | 6 | Granules | Sr$_2$P$_2$O$_7$ | 30.7 | 9.0 | 98.4 | 340 | HEP |
| 17 | 6 | Granules | Sr$_2$P$_2$O$_7$ | 41.0 | 9.0 | 99.2 | 360 | HEP |
| 18 | 7 | Granules | Sr(H$_2$PO$_4$)$_2$ | 24.7 | 4.4 | 95.5 | 320 | AEP |
| 19 | 7 | Granules | Sr(H$_2$PO$_4$)$_2$ | 6.7 | 0.6 | 99.6 | 320 | AEP |
| 20 | 8 | 25% Coated Spheres | Sr(H$_2$PO$_4$)$_2$ | 22.0 | 3.6 | 98.9 | 320 | HEP |
| 21 | 8 | 25% Coated Spheres | Sr(H$_2$PO$_4$)$_2$ | 10.9 | 18.3 | 91.1 | 320 | AEP |

[1]Analysis of catalyst after reaction to produce TEDA indicates the formation of a minor amount of SrP$_2$O$_7$.

TABLE 3

| Catalyst of Control | Form | Nominal Formulation | TEDA Yield, Wt. % | PIP Yield, Wt. % | Conversion Mol. % | Temp., °C. | Feed |
|---|---|---|---|---|---|---|---|
| 2 | 25% Coated Spheres | SrHAsO$_4$ | 4.6 | 6.2 | 36.2 | 340 | HEP |
| 2 | 25% Coated Spheres | SrHAsO$_4$ | 1.2 | 1.6 | 43.5 | 360 | AEP |
| 3 | Granules | SrSO$_4$ | 2.1 | 27.3 | 36.4 | 360 | HEP |
| 4[2] | Granules | AlPO$_4$ | 28.4 | 6.0 | 100 wt. % | 400 | HEP |
| 5[3] | Granules | AlPO$_4$ | 33.9 | 26.7 | 83 wt. % | 375 | AEP |

[2]Data obtained from Example II of U.S. Pat. No. 3,297,701.
[3]Data obtained from Example XXI of U.S. Pat. No. 3,297,701.

EXAMPLE 22

2000 grams of Sr(NO$_3$)$_2$ were dissolved in 2000 mls of deionized water and the solution diluted to 4000 mls with deionized water after dissolution of the Sr(NO$_3$)$_2$ was complete.

In another container, 1342.3 grams of Na$_2$HPO$_4$ were dissolved in 2000 mls of deionized water. After solution of the Na$_2$HPO$_4$ was complete, the solution was diluted to 4000 mls with deionized water. The pH of this solution was approximately 8.8.

Precipitation of SrHPO$_4$ was effected by slowly adding the Na$_2$HPO$_4$ solution of the Sr(NO$_3$)$_2$ solution with rapid stirring. The white SrHPO$_4$ precipitated rapidly from solution forming a rather thick slurry. This slurry was mixed for one hour, after which time the pH was measured to be about six.

The solid SrHPO$_4$ was recovered by filtering on an eight frame filter press using cloth filters. It was washed with deionized water. After filtering and washing, the solid was dried in a circulating hot air oven at 250° F. for four hours. The yield of SrHPO$_4$ was 1680 grams. The solid was wetted and formed into pellets by extrusion through a 3.1 mm die plate and cutting the extrudates to about ¼ inch in length. After drying the extrudate at 250° F. for four hours in a circulating hot air oven, they were heat treated at 662° F. for two hours in a 20% steam, 80% air atmosphere.

EXAMPLE 23

The catalyst of Example 22 was tested in the conversion of crude HEP to TEDA. The reaction was carried out at atmospheric pressure, at a liquid hourly space velocity of 0.3 and at the temperatures indicated in Table 4 below.

TABLE 4

| | Initial | After 78 Days |
|---|---|---|
| Bed Temp., °C. | 360 | 368 |
| HEP Conversion, wt. % | 99+ | 99+ |
| TEDA Yield, wt. % | 40.5 | 43.0 |
| Piperazine Yield, wt. % | 13.5 | 18.5 |

EXAMPLE 24

The catalyst of Example 22 was tested for the conversion of diethanolamine to TEDA. The test was carried out at 370° C. using a feed consisting of diethanolamine and water (2.0:1.0 mole ratio) pumped into the reactor at a rate of 4.4 liquid cc/hr along with helium diluent at a rate of 25 cc/minute. The diethanolamine was converted to TEDA as the only recovered product.

EXAMPLE 25

A 64% by weight solution of N-aminoethyl piperazine in water was passed over a catalyst composition consisting essentially of SrHPO$_4$ at 380° C. and at a liquid hourly space velocity of 0.3 volumes of liquid per volume of catalyst. In a first pass operation there was obtained 96.8% conversion of the feed compound, obtaining a yield of 34.8% by weight (40.1 mol %) TEDA and 27.1% by weight (40.6 mol %) piperazine.

EXAMPLE 26

Morpholine was reacted with dimethylethanolamine in substantially stoichiometric proportions in the presence of water over SrHPO$_4$ catalyst at a temperature of 360° C. and at a LHSV of 0.3. The organic reaction product contained 27% of N-(2-dimethylaminoethyl)-morpholine (DMAEM); which has the structural formula:

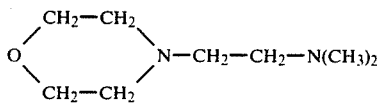

EXAMPLES 27-30

The SrHPO$_4$ catalyst of Example 5 was evaluated for the preparation of DMAEM with a feed mixture of morpholine (MOR), dimethylethanolamine (DMEA), distilled water, hydrogen and helium in the amounts shown below in Table 5 using the general procedure used in Examples 9-21 for the TEDA preparation. Specifically the condensation reaction was carried out at 340° C., 1 atmosphere of pressure and an LHSV of 0.21/hr. in the presence of 20 cc. of the SrHPO$_4$ catalyst granules. The results of these examples are summarized in Table 5 below.

TABLE 5

DMAEM PRODUCTION

| Example | Feed, Vol. % | Yield, Mol. % MOR | Conversion, Mol. % |
|---|---|---|---|
| 27 | MOR 40<br>DMEA 20<br>H$_2$O 20<br>He (20 cc/min) | 42 | 32 |
| 28 | MOR 40<br>DMEA 40<br>H$_2$O 20<br>He (20 cc/min) | 37 | 28 |
| 29 | MOR 60<br>DMEA 20<br>H$_2$O 20<br>He (20 cc/min) | 43 | 22 |
| 30 | MOR 20<br>DMEA 60<br>H$_2$O 20<br>He (20 cc/min) | 33 | 45 |

Other typical condensation reactions in which SrHPO$_4$, Sr$_2$P$_2$O$_7$ and Sr(H$_2$PO$_4$)$_2$ may be employed as catalysts include the formation of amines by amination of the corresponding alcohols with ammonia and the formation of polyamines from glycols and diamines.

It is believed that the key to the properties of SrHPO$_4$, Sr$_2$P$_2$O$_7$ and Sr(H$_2$PO$_4$)$_2$ as highly selective catalysts is due to the presence of a specific structure, which provides a narrow range of acidity. This narrow acidity range displayed by these catalysts may be optimum for promoting certain types of acid catalyzed reactions, in contrast to such catalysts as alumina, silica-alumina and the like which have acid sites of widely varying strength, and hence show relatively low selectivity for the desired reaction.

EXAMPLE 27

Diethyleneglycol was passed over SrHPO$_4$ catalyst in the presence of water at a temperature of 370° C. and at a contact time of 6.7 seconds. The feed contained 57 vol % diethylene glycol and 43 vol % H$_2$O. The reaction product contained 33 wt. % 1,4-dioxane, corresponding to a yield of 47 mol %.

EXAMPLE 28

The SrHPO$_4$ catalyst of Example 22 was tested for the conversion of 1,4-butanediol to tetrahydrofuran. The test was carried out at 350° C. using a feed consisting of 20 percent by volume of water and 80 percent by volume of 1,4-butanediol pumped to the tubular reactor at a rate of 4.4 cc/hr. Helium diluent was also fed at the rate of 30 cc/min. Under these conditions, the diol was completely converted to tetrahydrofuran.

What is claimed is:

1. In a method for synthesis of triethylenediamine from nitrogen-containing componds selected from the group consisting of hydroxyethylpiperazine, crude hydroxyethylpiperazine, N-aminoethyl piperazine, ethanolamines and substituted ethanolamines by condensation reactions in the presence of acidic catalyst, the improvement which comprises the use as such catalyst of a product selected from the group consisting of Sr$_2$P$_2$O$_7$, Sr(H$_2$PO$_4$)$_2$, mixtures thereof, and mixtures with SrHPO$_4$.

2. The method as defined in claim 1 wherein an inert gas is present during the conversion.

3. A method which comprises converting a substituted piperazine compound selected from the group consisting of hydroxyethylpiperazine and aminoethylpiperazine to triethylenediamine at a temperature in the range of about 285° C. to 420° C., and in the presence of a catalyst selected from the group consisting of the pyrophosphate and dihydrogen phosphate of strontium, mixtures thereof, and mixtures with strontium monohydrogen phosphate.

4. A method which comprises converting hydroxyethylpiperazone to triethylenediamine at a temperature in the range of about 340° to 400° C., and in the presence of a catalyst selected from the group consisting of the pyrophosphate and dihydrogen phosphate of strontium, mixtures thereof, and mixtures with strontium monohydrogen phosphate.

* * * * *